(12) United States Patent
Bialas et al.

(10) Patent No.: US 9,126,251 B2
(45) Date of Patent: Sep. 8, 2015

(54) METHODS FOR LASER CUTTING AND PROCESSING TUBING TO MAKE MEDICAL DEVICES

(71) Applicant: ADVANCED CARDIOVASCULAR SYSTEMS, INC., Santa Clara, CA (US)

(72) Inventors: Michael R. Bialas, Temecula, CA (US); Robert P. Barbier, Perris, CA (US); David Strauss, Temecula, CA (US); David Mackiewicz, Scotts Valley, CA (US); Pius Kienzle, Starzach (DE); Mihaela Baldi, Hechingen (DE)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 357 days.

(21) Appl. No.: 13/707,855

(22) Filed: Dec. 7, 2012

(65) Prior Publication Data
US 2013/0098131 A1   Apr. 25, 2013

Related U.S. Application Data

(60) Division of application No. 12/347,604, filed on Dec. 31, 2008, now Pat. No. 8,333,897, which is a continuation-in-part of application No. 11/756,305, filed on May 31, 2007, now Pat. No. 7,932,479.

(51) Int. Cl.
*B23P 13/00*     (2006.01)
*B23K 26/00*    (2014.01)
*B23K 28/02*    (2014.01)
*B21D 7/16*      (2006.01)
*B23K 26/16*    (2006.01)
(Continued)

(52) U.S. Cl.
CPC . *B21D 7/16* (2013.01); *B23K 26/00* (2013.01); *B23K 26/0093* (2013.01); *B23K 26/16* (2013.01); *B23K 26/38* (2013.01); *B23K 28/02* (2013.01); *B23P 13/00* (2013.01); *A61F 2/91* (2013.01); *B23K 2201/06* (2013.01); *Y10T 29/49995* (2015.01)

(58) Field of Classification Search
CPC .... B23P 13/00; B23K 26/00; B23K 26/0093; B23K 28/02
USPC ............... 29/423, 283.5; 219/121.68, 121.69; 72/340, 47, 283
See application file for complete search history.

(56) References Cited

U.S. PATENT DOCUMENTS 3,978,747 A * 9/1976 Lyon .................................. 83/18
4,052,784 A * 10/1977 Diepers et al. .................. 29/599
(Continued)

FOREIGN PATENT DOCUMENTS

DE         19831721 A1      1/2000

*Primary Examiner* — Samuel M Heinrich
(74) *Attorney, Agent, or Firm* — Fulwider Patton LLP

(57) ABSTRACT

A method for making a device includes providing a tubular member which will be formed into the device, masking at least a portion of the inner surface of the tubular member with a removable sacrificial material, selectively removing a portion of the tubular member and sacrificial material using a laser device, and mechanically removing the sacrificial material from the inner surface of the tubular member. Ultrasonic energy could be applied to a workpiece which is being laser cut to prevent any generated slag from welding itself to an exposed surface of the workpiece. A compressed fluid or gas, such as air, could be used to clean the surface of the laser-cut workpiece to remove slag formation which adheres to the surface of the cut workpiece.

6 Claims, 7 Drawing Sheets

(51) Int. Cl.
   *B23K 26/38* (2014.01)
   *A61F 2/91* (2013.01)

(56) References Cited

U.S. PATENT DOCUMENTS

| | | | |
|---|---|---|---|
| 5,609,055 A * | 3/1997 | Castricum | 72/49 |
| 5,797,999 A | 8/1998 | Sannomiya et al. | |
| 6,696,667 B1 | 2/2004 | Flanagan | |
| 6,865,810 B2 * | 3/2005 | Stinson | 29/896.6 |
| 2004/0097988 A1 | 5/2004 | Gittings et al. | |
| 2005/0119727 A1 * | 6/2005 | Fariabi | 623/1.16 |
| 2005/0145508 A1 | 7/2005 | Larsen et al. | |
| 2006/0251794 A1 | 11/2006 | Scheuermann | |
| 2006/0264914 A1 | 11/2006 | Furst et al. | |
| 2007/0073374 A1 | 3/2007 | Anderl et al. | |

* cited by examiner

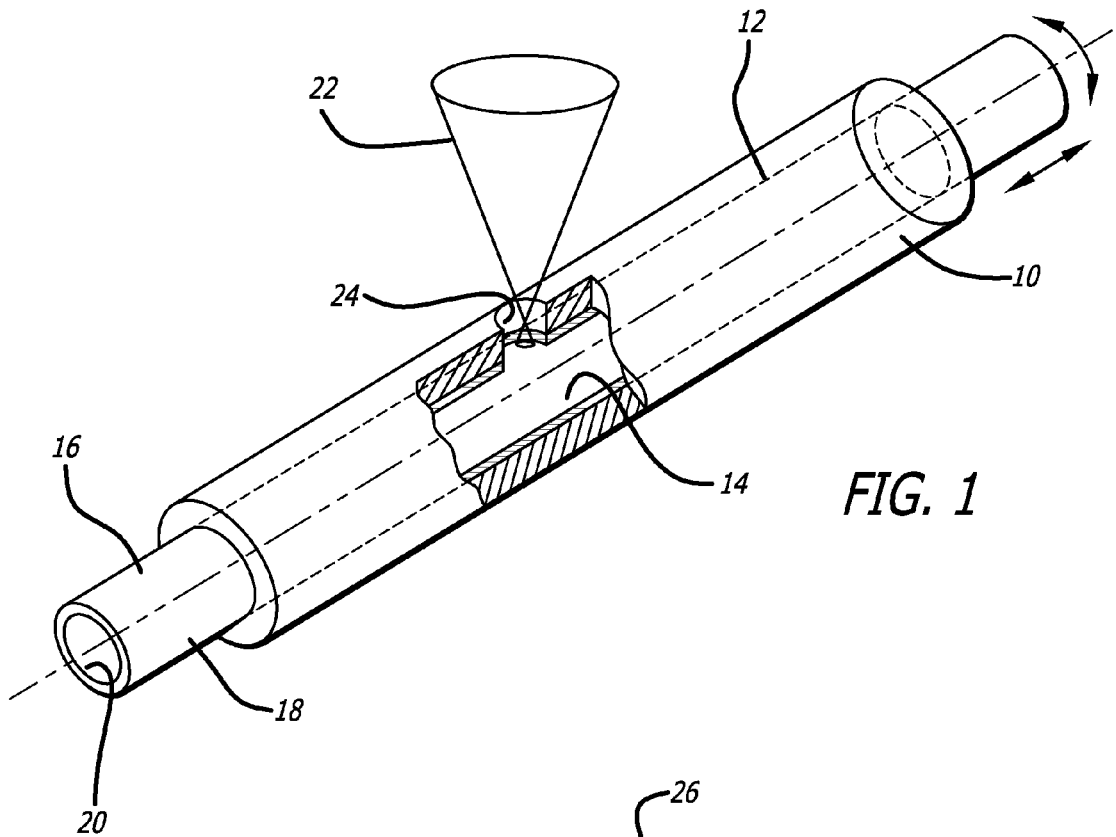
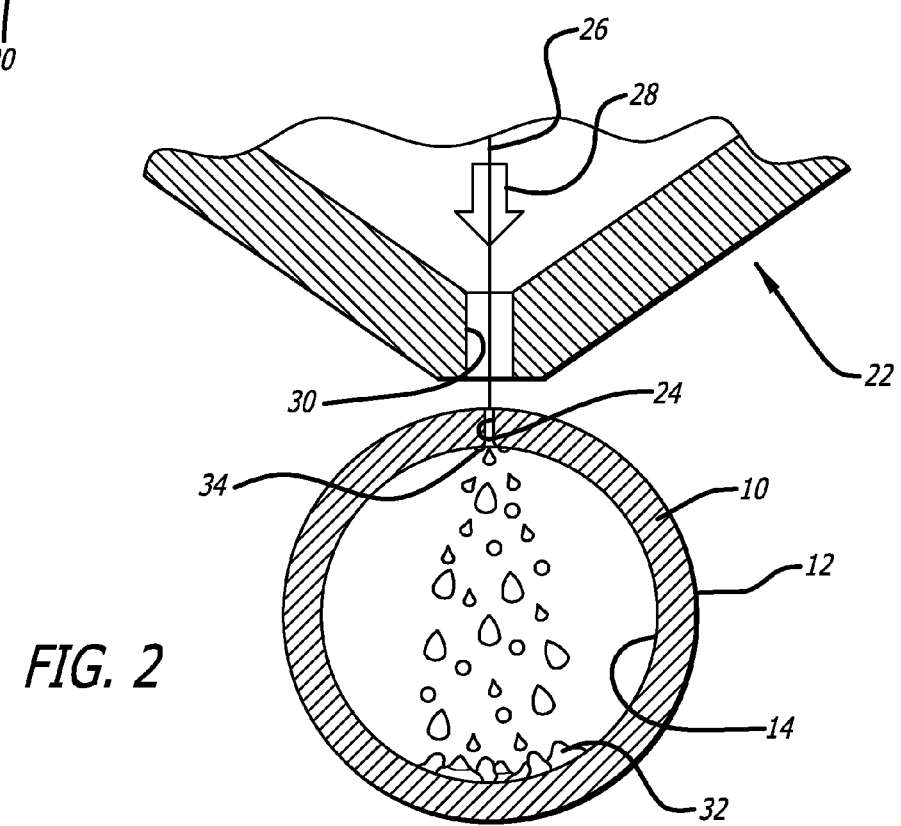
FIG. 1
FIG. 2

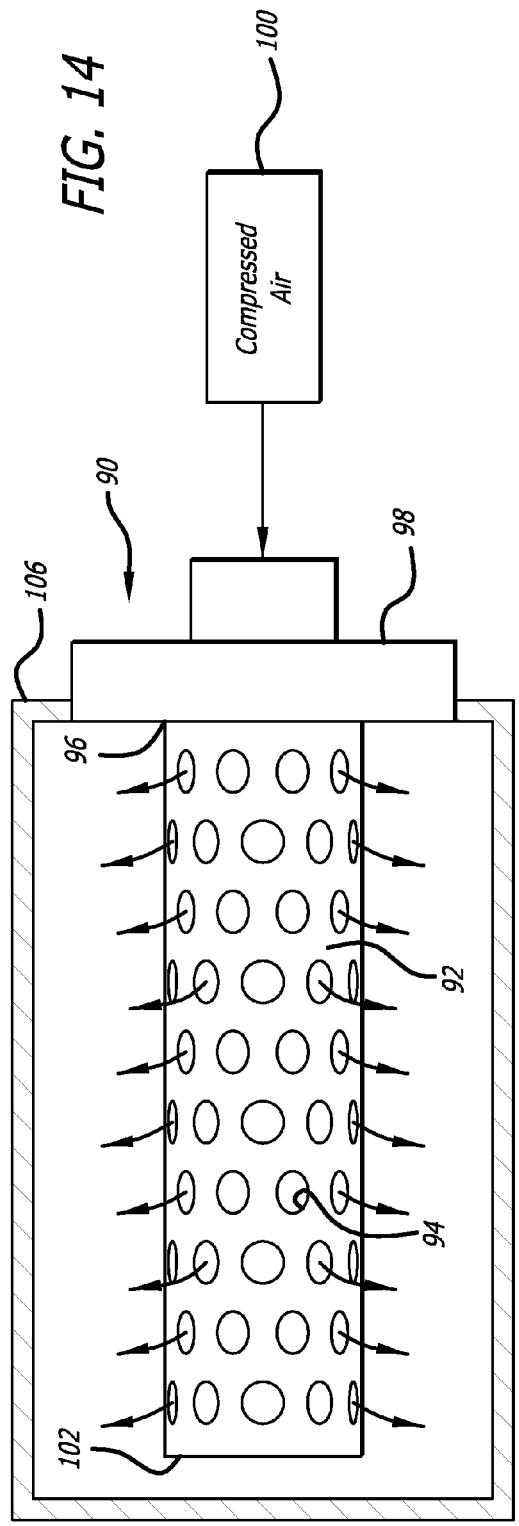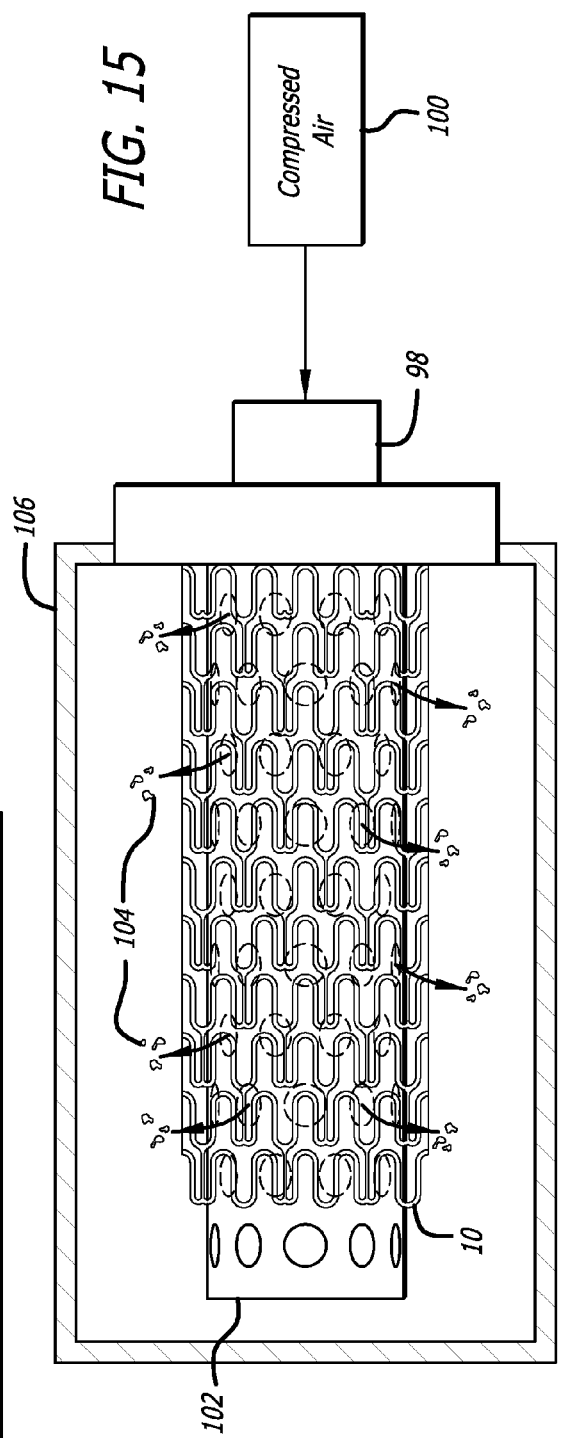

METHODS FOR LASER CUTTING AND PROCESSING TUBING TO MAKE MEDICAL DEVICES

CROSS-REFERENCE TO RELATED APPLICATIONS

This is a divisional application of U.S. Ser. No. 12/307,604 filed Dec. 31, 2008, which will issue as U.S. Pat. No. 8,333,897 and which is a continuation-in-part application of U.S. Ser. No. 11/756,305 filed on May 31, 2007 which issued as U.S. Pat. No. 7,932,479 on Apr. 26, 2011, the contents of each application are hereby incorporated by reference.

BACKGROUND OF THE INVENTION

The present invention relates generally to methods for laser cutting and processing a hollow workpiece, such as a length of tubing. The present invention is more particularly directed to methods for fabricating medical devices, such as, for example, expandable endoprostheses, commonly known as stents, using processes which help to prevent damage to the workpiece when cutting the workpiece with a laser apparatus and when later processing the cut workpiece.

Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the outcome of the procedure and reduce the possibility of restenosis.

Stents are generally cylindrically shaped devices which function to hold open, and sometimes expand, a segment of a blood vessel or other arterial lumen, such as a coronary artery. Stents are usually delivered in a compressed condition to the target site and then deployed at that location into an expanded condition to support the vessel and help maintain it in an open position.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self expanding stent formed from shape memory metals or super elastic nickel titanium alloys (Nitinol), which will automatically expand from a compressed state when the stent is advanced out of the distal end of the delivery catheter into the blood vessel.

Stents can be formed with strut patterns which when expanded have a large amount of open space, but when collapsed have little space between the often tortuously shaped struts forming the stent. One method of making a stent includes laser cutting a tubular member or tubing of suitable material to create the intricate strut patterns which define the structure of the stent. Laser cutting generally provides a precise method for forming these intricate strut patterns in the tubing used to form the stent. Such patterns require the tubing to be cut through one side of the wall of the tubing without cutting through the opposite side of the tubing.

In the past, laser apparatus utilizing pressured air (oxygen) have been used to cut the tubing. Generally, a laser beam locally heats the tubing material while pressurized air is blown through a small coaxial orifice directly onto the heated region in order to create a slot or "kerf" through the wall of the tubing.

Laser cutting of a length of tubing generally begins by focusing a laser beam on a targeted spot on the tubing. The spot is melted and is preferably vaporized, or at least partially vaporized, by the laser beam. Once the laser beam burns through the side wall of the tubing, the beam will usually continue to strike the opposite side wall of the tubing, and may begin to vaporize, or partially vaporize, the opposite side wall of the tubing. This undesirable burning or partial vaporization of the opposite sidewall is called "burn through" and can result in the weakening of opposite sidewall. In some cases, burn through may result in the workpiece being discarded. The melting and vaporization of the tubing also can form "recast" material, which is material from the tubing that has melted and resolidified on laser-cut surfaces. The recast material, also referred to as "dross," may include metal oxides and impurities which are undesirable in the manufacturing process since the recast material must be thoroughly removed from the surface of the stent. Oxidation can make a stent more susceptible to failure (e.g., cracking or fracture) during manufacturing or, if not completely removed, in use. Additionally, recast material can be particularly difficult to remove without damaging the thin struts created by the laser cutting operation. Therefore, both burn through and formation of recast material presents a formidable problem to the stent manufacturer.

The problems of laser cutting self-expanding stents made from a material such as Nitinol are further enhanced when pressurized air or oxygen is used to create the cut pattern. Because Nitinol is composed of about 50% titanium, a notoriously reactive metal, the titanium readily reacts with the oxygen in the air when heated. As a result, the material expelled during the cutting procedure is predominately comprised of metal oxides, most of which are trapped inside the tubing and adhere to the metallic inner surface of the Nitinol tube. Side walls of the slot or kerf also become oxidized during the cutting process, making the as-cut stent less ductile and thereby more susceptible to cracking or complete fracture during radial expansion or during other subsequent manufacturing steps. As a result, a laser cut Nitinol work piece must be carefully processed by a number of different cycles of chemical treatment, radial expansion, and heat stabilization to achieve the final stent size.

Any remaining oxidized wall material and other adhered oxide debris must first be removed in order to attain an acceptably smooth surface later during electropolishing. This additional clean up procedure can be achieved through a combination of automated grit blasting, manual grit blasting and chemical removal of oxide prior to electropolishing. Some methods require the physical removal of the recast material using a reamer or similar equipment and can often damage the thin struts of the stent. While electropolishing procedures can remove some recast material, often the recast material may be so heavily clad on the surface of the stent that not all of the recast material can be removed by this process. Additionally, the electropolishing process will remove material from the struts so it is important that only a small amount of the strut surface is actually removed. For example, if the electropolishing procedure is too long in duration, due to accumulated recast material, portions forming the struts of the stent may have too much material removed, resulting in a damaged or generally weakened stent.

Certain methods have developed to deal with the problem caused by burn through and the formation of recast material on the workpiece. One such method uses a continuous metal wire run through the tubular workpiece to create a "protective barrier" which somewhat helps to prevent the laser beam from striking the opposite sidewall of the tubing. Another system utilizes a liquid flushed through the workpiece as it is being cut. The fluid is usually fed through one end of the tubing and exits through the opposite end of the tubing, along with the newly formed openings in the wall of the tubing created by the laser. The liquid flushes away some of the recast material being created by the vaporization of the tubing. However, the presence of this liquid does not always completely block the laser beam, which can allow the inside wall of the tubing to be heated and damaged. Additionally, the use of liquid requires additional equipment for handling the liquid including discharge equipment, catch basins, waste disposal, and other processing equipment.

It has been anticipated that Nitinol stents could be laser cut using an inert gas such as argon or helium to prevent sidewall oxidation which would help prevent cracking or fracturing during subsequent processing. The absence of oxygen in the cutting process also will help to prevent the recast material from being oxidized. However, laser cutting Nitinol tubing utilizing pressurized argon gas typically cannot directly produce a finished stent because the expelled melted material formed during the cutting process can become "welded" to the inner wall of the tubing. This welded metallic build up could possibly be removed by later processing including reaming, drilling, electric discharge machining and the like but with difficulty and risk to the integrity of the workpiece.

What have been needed and heretofore unavailable are improved methods for reducing the adverse results caused by burn through along with the elimination of oxidation during the laser cutting process. Also, it would be beneficial to utilize additional equipment and processes to ease in subsequent cleaning, polishing and processing of the cut workpiece. The present inventions disclosed herein satisfy these and other needs.

SUMMARY OF THE INVENTION

The present invention is directed to methods for laser cutting a tubular workpiece which helps to reduce the number of post-cutting processing steps by preventing oxidation and preventing recast from adhering to the workpiece material during the laser cutting process. The present invention prevents oxidation of the workpiece by utilizing a laser apparatus that utilizes an inert gas, such as argon or helium, rather than air or oxygen, to create the slots or kerfs which form the pattern cut into the workpiece. The absence of oxygen in the cutting process thus prevents the workpiece from being oxidized during laser cutting. The present invention also utilizes a disposable, sacrificial mask which helps to prevent damage to the workpiece by covering the surface of the workpiece as it is being laser cut. The present invention is particularly beneficial in manufacturing intricately shaped devices from a hollow workpiece, such as a stent.

In one aspect of the invention, the disposable mask can be placed over at least a portion of the inner surface of the tubular member or tubing which is being laser cut. In the laser cutting process, recast material formed during the cutting process is forced through the kerf via the pressurized inert gas and is collected on the surface of the disposable mask, rather than on the inner surface of the tubular member. Tubing made from Nitinol can be laser cut using an inert gas without the risk of the recast material being welded onto the inner surface of the tubular member. During the cutting operation, both the tubular member and the disposable mask are simultaneously cut to the same pattern. During cutting, the expelled molten Nitinol collects on the inner surface of the disposable mask instead of directly on the inner surface of the tubular member, and afterward the expelled material and sacrificial mask can be removed because neither are strongly affixed to the inner surface of the Nitinol workpiece. Because the inert gas prevents oxidation of the sidewalls of the tubular member, the present invention allows the cut workpiece to be further processed with little or no need to grit blast tough oxidized material from the stent wall prior to electropolishing.

After the tubular member and sacrificial mask have been laser cut, there will be a build up of recast material formed along the bottom edges of the kerfs and elsewhere along the workpiece. Expelled molten material from the tubular member will collect on the inner surface of the sacrificial mask rather than being directly welded on to the inner surface of the tubular member. However, the recast material must still be removed from the laser-cut tubular member prior to electropolishing.

The present invention utilizes a variety of mechanical techniques to remove the sacrificial mask from the tubular member, along with a variety of chemical removal techniques which can be coupled with the mechanical techniques to quickly and cleanly remove the dross and sacrificial mask from the inner wall of the formed tubular member.

In one particular aspect of the present invention, the purely mechanical techniques for removing the dross and sacrificial mask is to attack the dross only, utilizing equipment which will grind, hone or bead-blast the dross only. Dross also can be removed utilizing a tool such as a wire brush or reamer. Another way to clean the lased tubular member would be to mechanically attack the sacrificial mask only. Similar mechanical techniques could be used to remove the sacrificial mask. Lastly, these same techniques could be used to mechanically attack both the dross and sacrificial mask. These various techniques provide simple but useful manufacturing steps to separate the lased tubular member from the sacrificial mask and dross.

In other aspects of the present invention, mechanical techniques to separate the components include employing different material properties between the lased tubular member and the sacrificial mask. For example, the tubular member and sacrificial mask could be made from different materials having different coefficients of thermal expansion. Application of heat or cold to the tubular member and sacrificial mask could then be used to break the sacrificial mask away from the lased tubular member.

In another mechanical procedure, a lased tubular member made from a self-expanding material, such as Nitinol, could be crushed and rolled to allow the tubular member to spring back to shape. Since the sacrificial mask is not superelastic, the crushing and rolling of the tubular member should break any connection between the sacrificial mask and the tubular member. Alternatively, the lased tubular member could be expanded, rather than being rolled, thereby causing the sacrificial mask to break away from the tubular member.

Still other removal procedures which can be implemented in accordance with the present invention include mechanically peeling the sacrificial mask from the lased tubular member or mechanically gripping and pulling/pushing the sacrificial mask out of the tubular member. Removal procedures could alternatively call for the tubular member/sacrificial mask to subjected to vibration, which would break the sacrificial mask from the tubular member.

In another aspect of the present invention, the procedure for removing the sacrificial mask and dross from the lased tubular member would utilize a combination of chemical removal techniques with mechanical removal techniques, such as the ones addressed above. For example, after cutting, the lased tubular member and sacrificial mask can be subjected to a chemical attack which would only attack the tubular member material therefore dissolving the dross. A chemical solution would be applied to both the tubular member and sacrificial mask. The application of the chemical solution is designed to primarily attack the tubular member, rather than the disposable mask material. As such, the chemicals are selected which preferably attack the material of the tubular member, leaving the sacrificial mask material generally unharmed. In one aspect of the invention, the chemical solution attacks the tubular member by etching it. It should be noted that the recast material (especially the thin connection between the sidewall and recast metal) has a very large surface area to volume ratio and therefore it is much more readily attacked by the chemical solution than the body of the tubular member itself. This process of applying a chemical solution which primarily attacks the material forming the tubular member eliminates or weakens much of the recast material formed in the kerfs and elsewhere, thereby allowing the tubular member and the sacrificial mask material to be more easily separated.

After the chemical solution has acted on the tubular member, the tubular member and the sacrificial mask material are mechanically separated. This mechanical separation causes any recast material that is still adhering to the tubular member to be broken off, leaving the inner surface of the tubular member virtually free of any recast material. The removal of the sacrificial material from the inner surface of the tubular member can be performed mechanically, for example, by devices which will break the recast material formed in the kerfs and elsewhere. The mechanical process of removing the sacrificial material from the tubular member can be performed, for example, by inserting a mandrel into the inner lumen of the disposable mask and twisting the sacrificial mask from the inner surface of the tubular member. Any of the mechanical techniques mentioned above could be implemented to remove the sacrificial mask and any remaining dross from the tubular member.

In another aspect of the present invention, the removal process would encompass the application of a chemical solution which attacks only the sacrificial mask, leaving the tubular member virtually unharmed. The chemical attack can either dissolve the sacrificial mask completely, or could just weaken the sacrificial mask. Any one of a number of mechanical procedures could then be implemented to remove any remaining portions of the sacrificial mask and dross.

The removal process could encompass the application of chemicals which attacks both the sacrificial mask and tubular member. In this aspect of the invention, a chemical solution could first be applied which attacks or dissolves only the dross, then a second chemical solution could be applied which attacks only the sacrificial mask. Alternatively, the chemical solution which only attacks the sacrificial mask could be applied first and later the chemical solution which attacks the dross could be applied. In yet another removal procedure, a chemical solution which simultaneously attacks both the tubular member and sacrificial mask could be applied. In one scenario, the chemical solution could completely dissolve the sacrificial mask and dross. Alternatively, if the solution only weakens the dross and sacrificial mask, any remaining dross and mask material could be mechanically removed using any of the mechanical techniques mentioned above.

In another aspect of the invention, the disposable mask can take the shape of a tubular sleeve that is placed snugly against the inside surface of the tubular member. The disposable mask preferably assumes the form of a thin wall tube whose outer diameter closely matches the inner diameter of the tubular member. Alternatively, the mask may be comprised of a flat foil that is rolled into a cylinder and then inserted into the tubular member. In other aspects, the disposable mask may be produced through the build-up of material such as by electroplating, plasma spray, physical vapor deposition, chemical vapor deposition and the like. However, the disposable mask material should not become metallurgically bonded or otherwise so strongly affixed to the tubular member that the two components cannot be easily separated from each other after laser cutting. Additionally, the disposable mask and the work piece should be made from dissimilar materials that do not easily weld or bond to one another.

In one particular aspect of the present invention, steel or stainless steel is used to form the disposable mask when the workpiece is being formed from binary nickel-titanium or a nickel-titanium alloy due to the inherent metallurgical incompatibility of these materials. The disposable mask also could be made from any suitable material capable of withstanding the temperatures of the expelled molten Nitinol material, for example, ceramics, metals, composites, or high temperature polymers.

In another particular aspect of the present invention, carbon steel can be used to form the disposable mask when the workpiece is being formed from binary nickel-titanium or a nickel-titanium alloy due to the inherent metallurgical incompatibility of these materials. In one aspect, the disposable mask can be made from a carbon steel strip which is rolled or coiled into a sleeve that fits within the lumen of the tubular member. The strip of carbon steel creates a coiled sleeve which can expand radially within the lumen of the tubular member to ensure that a tight fit is made between the surfaces of the coiled sleeve and tubular member.

In another aspect of the present invention, the coiled sleeve and tubular member could be selectively lased removing a portion of the tubular member and coiled sleeve. After the laser cutting step, an acid etchant solution could be applied to the tubular member and coiled sleeve to erode the coiled sleeve. Any portion of the coiled sleeve which remains after the laser cutting would be eroded by the acid etchant. In another aspect, the acid etchant could be heated prior to application of the acid etchant to the tubular member and coiled sleeve. The acid etchant can be a mixture of hydrofluoric acid and nitric acid. In one aspect, the application of the acid etchant can be performed by placing the tubular member and coiled sleeve into a bath containing the acid etchant The tubular member can be further processed by rinsing it with water and placing it in an ultrasonic bath containing alcohol.

In another aspect of the present invention, the process of making the device includes placing a sleeve made from a removable sacrificial material within the lumen of the tubular sleeve and co drawing the tubular member and sleeve together. In this aspect of the invention, the co drawing causes the surfaces of the sleeve and tubular member to come close together such that small spaces or gaps between the surfaces are eliminated or greatly reduced. The co drawing of the tubular member and sleeve should be controlled to prevent the surfaces from molecularly bonding to each other. The tubular member and sleeve could then be laser cut with any remaining portion of sleeve being removed from the tubular member. In one aspect, the removal of any remaining portion of the sleeve can be done mechanically. In another aspect, the removal can be done chemically. In one particular aspect, any remaining portion of the sleeve cab be chemically removed from the tubular member by applying a chemical solution to the tubular member and sacrificial material for a time duration in which the chemical solution primarily attacks the sacrificial material.

The pressurized inert gas used with the laser apparatus could be argon or helium as these two inert gases are economical and commercially available. However, it should be understood that the laser cutting of the tubular metallic work piece could utilize any inert or nonreactive, oxygen-free gas to prevent oxidation during the cutting process.

The use of the present method in forming a medical device, such as a stent, helps to minimize the need for grit blasting or otherwise chemically removing the oxidized cast material prior to electropolishing since air or oxygen is no longer used in the laser cutting process. The use of the inert gas eliminates the possibility that the sidewalls of the tubular member and recast material will become oxidized during laser cutting. As a result, the elimination of sidewall oxidation helps to prevent cracking or fracturing of the stent during use and eliminates some of the subsequent processing which would be otherwise be needed to remove the oxidized material from the tubular member. As a result, the formed workpiece can be sent for electropolishing without the need for additional processing which could break or irreparably damage the fragile struts which form the stent.

In yet another aspect of the present invention, the process of making the device includes applying ultrasonic energy to the tubular member as it is being laser cut into the desired shape of the workpiece. The application of ultrasonic energy to the tubular member helps top prevent slag from solidifying on the inner surface of the tubular member. The application of ultrasonic energy to the tubular member could be performed when the tubular member is being cut utilizing conventional laser cutting techniques already known in the art or could be used in conjunction with the novel sacrificial masks and processes disclosed herein.

In one particular aspect of the present invention, ultrasonic energy could be applied using an ultrasonic source, such as an ultrasonic transducer which includes a bushing that contacts the outer surface of the tubular member as it is being cut. The use of ultrasonic energy can be used in any laser cutting operation in which slag is formed and becomes problematic to the manufacturer since the slag will become deposited on a surface of the tubular member and will be required to be removed during subsequent processing.

In yet another aspect of the present invention, cleaning and polishing of the cut workpiece can be accomplished without application of excessive forces which could otherwise damage the often intricately cut workpiece. In this aspect, the cut tubular workpiece could be subjected to compressed air which will cause any slag affixed to the surface to be quickly removed. In one particular aspect, a mounting fixture having a number of outlet openings could be utilized to supply compressed air in the form of individual jets to the surface of the tubular workpiece. A compressed air supply would be connected to the mounting tube to supply the compressed air to the mounting fixture. The tubular workpiece would be slidable over the mounting fixture to allow the surface to be subjected to multiple jets of compressed air which will break most bonds between the slag and the surface of the workpiece. This process may eliminate the need to apply excessive force to the workpiece to break the slag from the surface. As a result, a greater yield of finished workpieces can be accomplished in less time that is normally needed to remove the slag using manual techniques.

These and other advantages of the present invention become more apparent from the following detailed description of the invention, when taken in conjunction with the accompanying exemplary drawings.

BRIEF DESCRIPTION OF THE DRAWINGS

FIG. 1 is a perspective view showing a schematic of a method of making a device, such as a stent, from a tubular member using a laser device which uses an inert gas to assist in the cutting process;

FIG. 2 is an end view showing the resulting formation of recast material on the inside surface of a tubular member when the laser cuts one side of the tubular member;

FIG. 14 is a top view showing a compressed air mounting fixture which discharges multiple jets of air to clean a tubular workpiece; and FIG. 15 is a top view showing a laser-cut tubular workpiece disposed on the compressed air mounting fixture of FIG. 14.

DETAILED DESCRIPTION OF THE PREFERRED EMBODIMENTS

Figure 3:
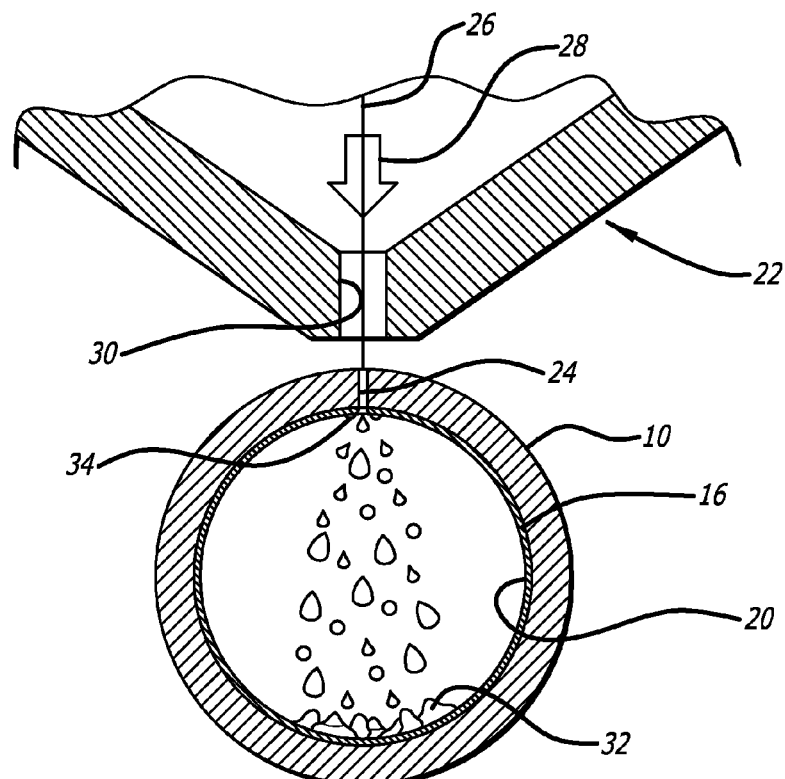
FIG. 3 is schematic side view showing the laser cutting of the tubular member mounted on a disposable sacrificial mask.

Referring now to the drawing in which reference numerals represent like or corresponding elements across the drawings, and particularly FIGS. 1 and 3-5, a method of making a device from a hollow tubular member 10 is generally disclosed. The present invention relates generally to methods for laser cutting a length of hollow tubing, or as is it referred to herein a "tubular member," to form a device, typically a medical device, such as a stent. While most workpieces formed in accordance with the present invention are in the form of a tubular member having a circular cross section, the tubular member could have a non-circular cross section as well. For example, the tubular member could have a rectangular, oval, square, and the like cross section, if desired. Moreover, the invention is not limited to forming stents and has a wide application with respect to other laser cut medical devices and non-medical products, particularly products which require a high precision pattern that is cut utilizing a laser cutting process.

Referring specifically to FIG. 1, in one particular form of the present invention, the method includes providing a tubular member 10 which will be formed into the finished device. The tubular member 10 has an outer surface 12 along with an inner surface 14. The tubular member 10 is made from a particular material suitable for the finished device and is to be laser cut, as will be described herein, to generally form the desired pattern and shape of the finished workpiece. The present invention is particularly useful in cutting a tubular member made from a nickel-titanium alloy (Nitinol) or a ternary nickel-titanium alloy such as nickel-titanium-platinum. When a stent is being fabricated, the tubular member will be laser cut to remove portions of the tubular member to create the desired strut patterns of the stent. It should be appreciated that additional processing of the workpiece may be needed after initial laser cutting to achieve the final finished product.

As can be seen in FIG. 1, the tubular member 10 is shown in contact with a disposable mask made from a sacrificial material that will be simultaneously laser cut with the tubular member 10, but will be later removed in subsequent processing. This disposable mask, shown in this particular embodiment of the invention as a masking sleeve 16, is placed within the tubular member 10 to cover or mask at least a portion of the inner surface 14 of the tubular member 10. This masking sleeve 16 includes an outer surface 18 and an inner surface 20. The masking sleeve 16 is placed snugly against the inside surface 14 of the tubular member and can be later removed from contact with the tubular member 10. The disposable mask can be formed as a thin wall tube whose outer diameter closely matches the inner diameter of the tubular member 10. Generally, the disposable mask can have the same length, or can be larger or smaller than the length of the tubular member, depending, of course, on the amount of laser cutting to be performed on the tubular member 10. As is depicted in FIG. 1, the length of the masking sleeve 16 is longer that the length of the tubular member 10.

The method further includes the cutting of the tubular member 10 and masking sleeve 16 by laser cutting apparatus 22, shown schematically in the drawing figures. In one aspect of the present invention, the laser cutting apparatus 22 utilizes a pressurized inert gas, such as argon or helium, rather than air or oxygen, to create the slots or kerfs 24 extending through the wall of the tubular member 10 and masking sleeve 16. In the method of the present invention, both the tubular member 10 and masking sleeve 16 are cut simultaneously by the laser cutting apparatus 22. Generally, as is schematically depicted in FIG. 3, a laser beam 26 locally heats the tubular member 10 and masking sleeve 16 while the pressurized inert gas, depicted by arrow 28, is blown through a small coaxial orifice 30 directly onto the heated region in order to create the slots or kerfs 24.

Laser cutting of the tubular member 10 and masking sleeve 16 generally begins by focusing a laser beam on a targeted spot on the tubing. The spot is melted by the laser beam while the pressurized inert gas forces the molten material through the walls of the tubular member and masking sleeve 16 to form the kerf 24. The tubular member 10 and sleeve 16 are moved by an automated mechanism of the laser cutting apparatus to create the desired pattern. Once the laser beam burns through the side wall of the tubular member 10 and masking sleeve 16, the laser beam could possibly continue to strike the opposite inside surface of the tubular member. However, the masking sleeve 16 covers the inner surface of the tubular member 10, thus preventing any damage to the tubular member. In the laser cutting process, recast material 32 which is forced through the kerf via the pressurized inert gas is collected as a disposable mass on the masking sleeve 16, rather than being "welded" to the inner surface 14 of the tubular member 10. In this aspect of the invention, the masking sleeve 16 forms a protective barrier for the inner surface 14 of the tubular member 10. FIG. 2 shows how the recast material would strike and damage the inner surface of the tubular member 10 if a disposable mask is not present. Also, since the inert gas prevents sidewall oxidation, the method of the present invention allows the cut work piece to be processed downstream without the need for substantial automated or manual grit blasting prior to electropolishing.

Figure 4:
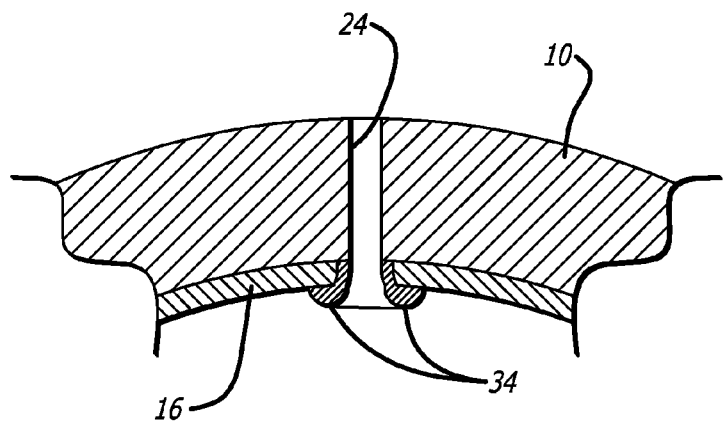
FIG. 4 is a side elevational view showing the resulting build up of recast material or "slag" along the bottom edge of the slot or kerf formed on the tubular member which must be removed prior to electropolishing.
Figure 5:
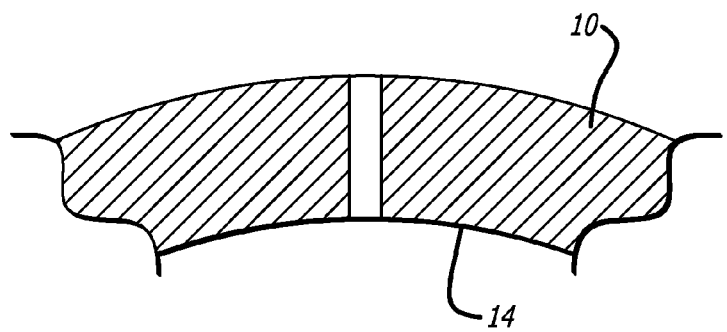
FIG. 5 is a side elevational view showing the disposable mask and recast material removed from the inner surface of the tubular member.

As is best depicted in FIG. 4, the laser cutting process not only results in the formation of recast material 32 disposed as bulk waste on the inner surface 20 of the masking sleeve 16, but also results in the formation of recast droplets 34 near the lower portion of the kerf 24. These recast droplets 34 cause portions of the tubular member 10 and masking sleeve 16 to somewhat bond together, forming an unwanted melded structure which must be removed from the tubular member 10 before additional processing proceeds. These recast droplets 34 are primarily solidified droplets of the material forming the tubular member 10.

The present invention utilizes a variety of mechanical techniques to remove the sacrificial mask and dross from the tubular member, along with a variety of chemical removal techniques which can be coupled with these mechanical techniques to quickly and cleanly remove the dross and sacrificial mask from the inner wall of the laser cut tubular member.

In one particular post-cutting procedure, the purely mechanical techniques for removing the dross and sacrificial mask is to attack the dross only, utilizing equipment which will grind, hone or bead-blast the dross only. For example, dross also can be removed utilizing a tool such as a wire brush or reamer. Another way to clean the lased tubular member would be to mechanically attack the sacrificial mask only. Similar mechanical removing techniques could be used to remove the sacrificial mask. Lastly, these same techniques could be used to mechanically attack both the dross and sacrificial mask. These various techniques provide simple but useful manufacturing steps to separate the lased tubular member from the sacrificial mask and dross.

The process of mechanically separating the disposable mask from the tubular member can use, for example, any type of device which will break the recast droplets and the contact between the surfaces of the tubular member and disposable mask. For example, the mechanical process of removing the sacrificial material from the tubular member can be performed by inserting a mandrel (not shown) into the lumen of the masking sleeve. The mandrel can be twisted causing the disposable mask to break contact with the inner surface 14 of the tubular member 10. The twisting action of the mandrel helps to peel the disposable masking material from the inner surface of the tubular member and break the bond created by the recast material and droplets. The surface of the mandrel could include prongs, flutes, knurling or other friction enhancing structure which increases frictional contact between the mandrel and disposable mask. It should be appreciated that other means for mechanically removing the disposable mask from the tubular member can be utilized in accordance with the present invention.

Another particular mechanical technique for removing the sacrificial mask and dross from the tubular member would require the separation of the components by employing different material properties between the lased tubular member and the sacrificial mask. For example, the tubular member and sacrificial mask could be made from different materials having different coefficients of thermal expansion. For example, heat or coldness could be applied to the cut work piece to cause the tubular member to either expand or contract, which should break the sacrificial mask away from the lased tubular member. Alternatively, the sacrificial mask could be made from a material which will expand or contract upon application of heat or coldness to cause the mask to break away from the tubular member.

In another mechanical procedure, a lased tubular member made from a self-expanding material, such as Nitinol, could be crushed and rolled to allow the tubular member to spring back to shape. The sacrificial mask could be made from a material which is comparatively not very elastic, so that the crushing and rolling of the tubular member should break any connection between the sacrificial mask and the tubular member. Alternatively, the lased tubular member could be expanded, rather than being rolled, which again should cause the sacrificial mask to break away from the tubular member.

Still other removal procedures which can be implemented in accordance with the present invention include mechanically peeling the sacrificial mask from the lased tubular member or mechanically gripping and pulling/pushing the sacrificial mask out of the tubular member. A reamer or mandrel could be used to grip the inside surface of the sacrificial mask to allow a technician to pull or push the mask from the tubular member. Other tools could be implemented as well to accomplish this type of mechanical removal. Additionally, removal procedures could alternatively call for the laser cut tubular member/sacrificial mask to subjected to vibration, which would break the sacrificial mask from the tubular member.

In another aspect of the present invention, the procedure for removing the sacrificial mask and dross from the lased tubular member would utilize a combination of chemical removal techniques with mechanical removal techniques, such as the ones addressed above, to achieve a clean workpiece which is ready for electropolishing. For example, after cutting, the lased tubular member and sacrificial mask can be subjected to a chemical attack which would only attack the tubular member itself, i.e. the dross. A chemical solution would be applied to both the tubular member and sacrificial mask. The application of the chemical solution is designed to primarily attack the tubular member, rather than the disposable mask material. As such, the chemicals are selected which preferably attack the material of the tubular member, leaving the sacrificial mask material generally unharmed. In one aspect of the invention, the chemical solution attacks the tubular member by etching it.

The process for removing the recast material and droplets from the tubular member requires a chemical solution to be applied to both the tubular member 10 and masking sleeve 16. The chemical solution can be directly applied to the tubular member 10 and masking sleeve 16 or the components could be dipped into a bath containing the chemical solution. The chemical solution is designed to primarily attack the tubular member 10, leaving the masking sleeve unharmed. It should be noted that the recast droplets 34 have a very large surface area to volume ratio and therefore they are much more readily attacked by the chemical solution than the larger body of the tubular member 10 itself. This process of applying a chemical solution which primarily attacks the tubular member 10 eliminates or weakens much of the recast droplets 34, thereby allowing the tubular member 10 and the masking sleeve 16 to be more easily separated.

After the chemical solution has acted on the tubular member, the tubular member and the sacrificial mask material can be further processed, if needed, using mechanically separation procedures. This mechanical separation causes any recast material that is still adhering to the tubular member to be broken off, leaving the inner surface of the tubular member virtually free of any recast material. After the chemical solution is applied to the tubular member 10 and masking sleeve 16 and the recast material is weakened, the tubular member and the masking sleeve 16 should be relatively easy to separate using mechanical techniques. Since the masking sleeve is virtually unharmed by the chemical solution, it remains stiff and capable of breaking the recast material formed at the kerfs when twisted away from the tubular member. Any recast material or droplets 34 that still adhere to the tubular member 10 will be broken off, leaving the inner surface 14 of the tubular member 10 virtually free of any recast material.

The removal of the sacrificial material from the inner surface of the tubular member can be performed mechanically, for example, by devices which will break the recast material formed in the kerfs and elsewhere. The mechanical process of removing the sacrificial material from the tubular member can be performed, for example, by inserting a mandrel into the inner lumen of the disposable mask and twisting the sacrificial mask from the inner surface of the tubular member. Any of the mechanical techniques mentioned above could be implemented to remove the sacrificial mask and any remaining dross from the tubular member, after the chemical application has been completed.

In another aspect of the present invention, the process of removing the mask and dross from the tubular member would encompass the application of a chemical solution which attacks only the sacrificial mask, leaving the tubular member virtually unharmed. The chemical attack can either dissolve the sacrificial mask completely, or could just weaken the sacrificial mask. Any one of a number of mechanical procedures could then be implemented to remove any remaining portions of the sacrificial mask and dross.

The removal process could encompass the application of chemicals which attacks both the sacrificial mask and tubular member. In this process, a chemical solution could first be applied which attacks or dissolves only the dross. Thereafter, a second chemical solution could be applied which attacks only the sacrificial mask. Alternatively, the chemical solution which only attacks the sacrificial mask could be applied first and later the chemical solution which attacks the dross could be applied. In yet another removal procedure, a chemical solution which simultaneously attacks both the tubular member and sacrificial mask could be applied. In one scenario, the chemical solution could completely dissolve the sacrificial mask and dross, eliminating the need for any further mechanical separation. Alternatively, if the chemical solution only weakens the dross and sacrificial mask, any remaining dross and mask material could be mechanically removed using any of the mechanical techniques mentioned above.

The use of the present method in forming a medical device, such as a stent, reduces the amount of grit blasting or chemical removal due to the lack of oxidized cast material since air or oxygen is no longer used in the laser cutting process. Again, the use of the inert gas eliminates the possibility that the sidewalls or the recast material will be oxidized during the laser cutting step. As a result, the elimination of sidewall oxidation helps to prevent cracking or fracturing of the stent during use and reduce or even eliminates some of the subsequent processing which would be otherwise utilized in order to remove the oxidized material from the tubular member. As a result, the formed stent can be sent for electropolishing without the need for additional processing, or with only a minimal amount of mechanical processing, which reduces the chance of breaking or irreparably damaging the often fragile struts forming the stent.

Although the sacrificial mask is disclosed herein as a disposable masking sleeve, it should be appreciated that other forms and configurations of a disposable sacrificial mask could be used in accordance with the present invention. For example, the mask may be comprised of a flat foil that is rolled into a cylinder and then inserted into the tubular member. Additionally, the disposable mask could be produced through the build-up of material on the inner surface of the tubular member by such methods as electroplating, plasma spraying, physical vapor deposition, chemical vapor deposition and the like. However, it is important that the disposable sacrificial mask material does not become metallurgically bonded or otherwise so strongly affixed to the tubular member that the two components cannot be easily separated from each other after laser cutting and the application of the mechanical and/or chemical processing of the cut workpiece. Thus, the disposable mask and the tubular member should preferably be made from dissimilar materials that do not easily weld or bond to one another. In one particular method of the present invention, steel or stainless steel can be used to form the disposable mask when a Nitinol tubular member is being fabricated because of their inherent metallurgical incompatibility. For example, the disposable mask could be formed from any material capable of withstanding the temperatures of the expelled molten material, such as ceramics, metals, composites, or high temperature polymers. Other suitable metals include steel, copper, magnesium, nickel, cobalt, molybdenum, tantalum, niobium, titanium, zirconium, tin, iron, or any other alloy based on these metals.

The pressurized inert gas used with the laser cutting apparatus include argon or helium as these two inert gases are economical and commercially available. However, it should be understood that the laser cutting apparatus could utilize any inert gas to prevent the work piece from oxidizing. Since argon and helium gases are more readily available commercially, these inert gases may serve to be more economical from a cost standpoint.

One particular method of chemically attacking the tubular member results in the material forming a tubular member to be etched away to weaken any recast material remaining on the workpiece. In this particular method of the present invention, a nickel-titanium or a ternary nickel-titanium alloy is the material used to form the tubular member and stainless steel is used to form the disposable mask. The tubular member and mask can be immersed in a solution of approximately 3% hydrofluoric acid (HF) and 50% nitric acid to chemically etch the recast material formed by the tubular member to help break the strength of the bond created by the recast material. The acid can rapidly etch away at the nickel-titanium alloy while the stainless steel disposable mask remains relatively undamaged. In this aspect of the invention, the acid will leave the stainless steel material relatively unharmed. The submersion of these two components in the hydrofluoric acid can be for a time duration from approximately 30-45 seconds, after which the components are removed. If needed, the mechanical process of removing the disposable mask from the tubular member can then be performed. In another variation, a steel sleeve could be used and the aforementioned HF-nitric solution could be used to simultaneously and completely dissolve both the steel sleeve and nitinol dross in only 10-20 seconds. This embodiment is particularly useful when the workpiece is particularly long or delicate therefore making the mechanical removal of the sleeve difficult. It should be appreciated that other chemical solutions could be utilized in accordance with the present invention. For example, the chemical solution can be acidic, alkaline, or any other chemically reactive agent which preferably attacks the tubular member rather than the disposable mask material or simultaneously attacks both. The strength of the chemical solution and the time duration that the chemical solution remains on the components will depend, of course, on the type of materials used for the tubular member and disposable mask and the type of chemical utilized.

Figure 8:
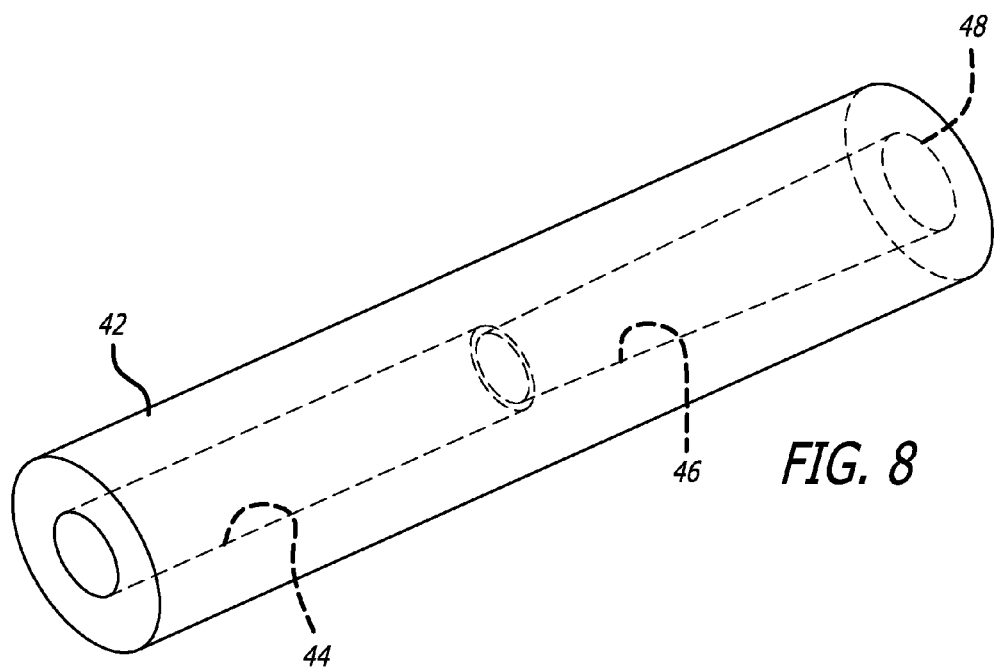
FIG. 8 is a perspective view of a tool which draws down the rolled carbon steel sleeve of FIGS. 6 and 7 in order to fit within a tubular member.
Figure 9:
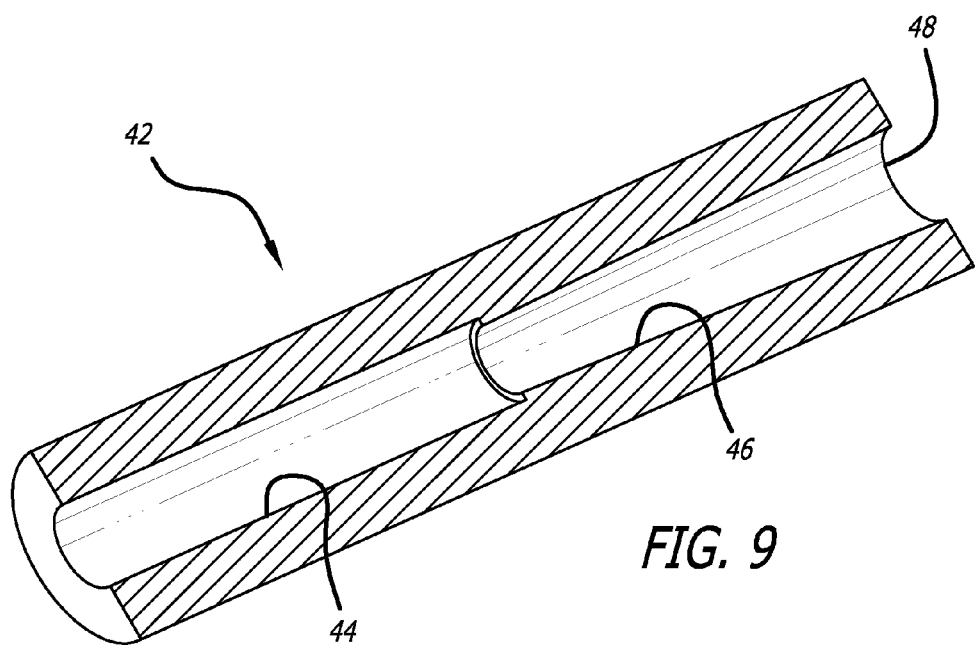
FIG. 9 is a cross-sectional view of the tool of FIG. 8.
Figure 10:
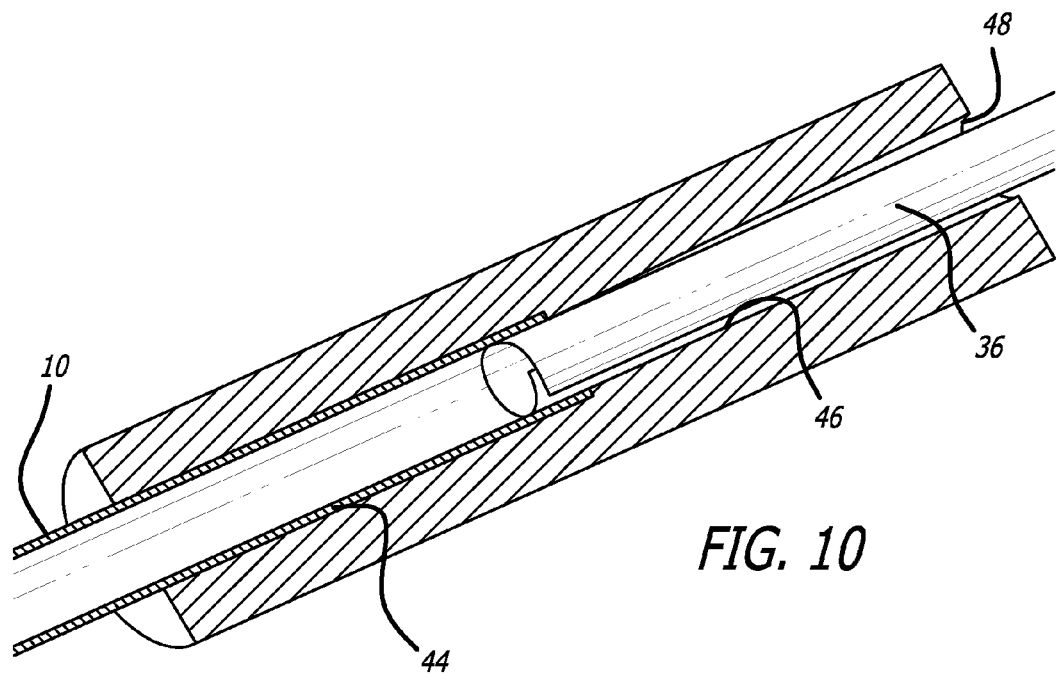
FIG. 10 is a cross-sectional elevational view showing the rolled sleeve of FIGS. 6 and 7 being drawn down by the tool of FIGS. 8 and 9 in order fit the rolled sleeve into a tubular member.

Referring now to FIGS. 6-10, the disposable mask can be made from a strip of material which is rolled or coiled into a sleeve 36. This coiled sleeve 36, in turn, fits within the lumen of the tubular member 10 (FIG. 10). The strip of carbon steel creates a coiled sleeve 36 having an outer surface 38 which contacts the inner surface 14 of the tubular member 10. The coiled sleeve 36 is biased somewhat so that it can expand radially within the lumen of the tubular member 10 to ensure that a tight fit is made between the surface 30 of the coiled sleeve 36 and the surface 14 of the tubular member 10. This coiled sleeve 36 can be used in any of the method disclosed herein.

Figure 6:
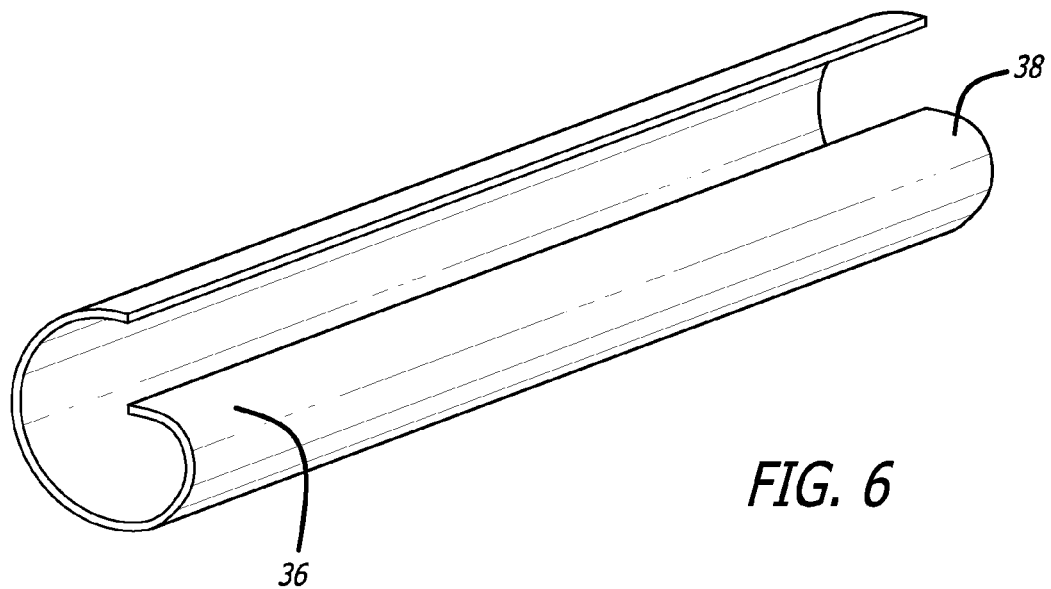
FIG. 6 is a perspective view of a carbon steel sleeve which is rolled to create a disposable sacrificial mask in accordance with the present invention.
Figure 7:
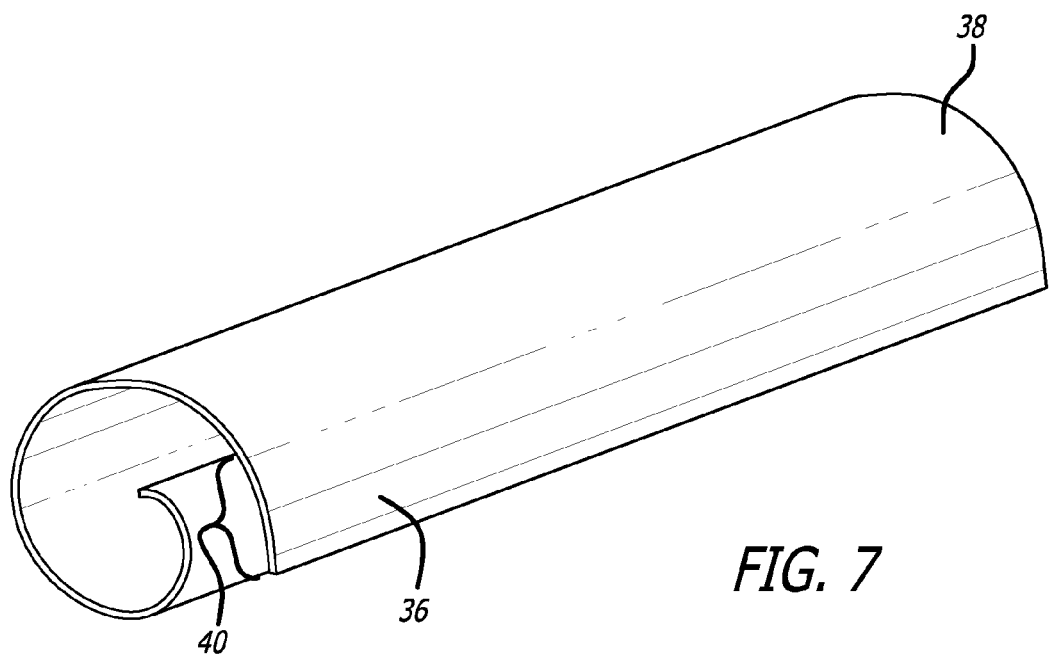
FIG. 7 is a perspective view of the rolled carbon steel sleeve of FIG. 6 which shows a portion of overlap of the sleeve.

As can be seen in FIG. 7, there is a slight overlap 40 of material forming the coiled sleeve 36. This overlap 40 allows the sleeve 36 to expand radially outward to contact the inner surface of variously sized tubular members. In this aspect, the coiled sleeve can be used in a number of tubular members having different diameters. In this fashion, the coiled sleeve will expand to the particular inner diameter of the tubular member in which it is placed. Thus, the use of a coiled sleeve eliminates the need to manufacture individually sized sleeves for use with particularly sized tubular member. Hence, one coiled sleeve can be placed in a number of different sized tubular members. While the particular embodiment of the coiled sleeve 36 of FIGS. 6 and 7 shows an overlap 40 ranging about 20° of the full 360° of the circle forming the diameter of the sleeve, it should be appreciated that more or less of an overlap 40 could be used on the coiled sleeve 36 as well. This overlap 40 represents the amount of material which overlaps when the coiled sleeve is in its maximum outside diameter. As will be discussed below, this maximum outside diameter can be reduced to a minimum outside diameter by applying force to coiled sleeve.

A tool 42, shown in FIGS. 8-10, can be used to place the coiled sleeve 38 within the lumen of the tubular member 10. This tool 42 is simply a structural member having two lumens extending therethrough. The first lumen 44, is used to hold the tubular member 10 as is shown in FIG. 10. The second lumen 46, is used to move the coiled spring into the lumen of the tubular member 10. In this regard, this second lumen may be tapered so that a larger diameter is located at the opening 48 through which the coiled sleeve is inserted. The second lumen tapers to a smaller diameter which causes the coiled sleeve to contract to a smaller diameter as it is further inserted into the second lumen 46. In turn, the smaller diameter of this second lumen 46 draws the coiled sleeve down to properly fit within the lumen of tubular member 10, as is shown in FIG. 10. A plunger (not shown) could be applied to the end of the coiled sleeve to help push the coiled sleeve 36 into the tubular member. Once the coiled sleeve is placed within the lumen of the tubular member 10, it will radially expand to create force that maintains tight contact between the surface 38 of the sleeve 36 and the inner surface 14 of the tubular member 10. It should be appreciated that other tools and methods could be utilized to place the coiled sleeve within the lumen of the tubular member.

In another particular aspect of the present invention, carbon steel can be used to form the coiled sleeve 36, although other material listed above could also be to create the sleeve. In one particular method of making a device, the coiled sleeve could be placed within the lumen of the tubular member. The coiled sleeve 36 and tubular member 10 could be selectively lased removing a portion of the tubular member and coiled sleeve. After the laser cutting step, an acid etchant solution could be applied to the tubular member and coiled sleeve to erode the coiled sleeve. Any portion of the coiled sleeve which remains after the laser cutting would be eroded by the acid etchant. The acid etchant could be heated prior to application of the acid etchant to the tubular member and coiled sleeve. The acid etchant can be a mixture of hydrofluoric acid and nitric acid. In one aspect, the application of the acid etchant can be performed by placing the tubular member and coiled sleeve into a bath containing the acid etchant The tubular member can be further processed by rinsing it with water and placing it in an ultrasonic bath containing alcohol.

In one particular example, a strip of 0.0003 inch thick carbon steel having a width of about 0.33 inches is rolled into a tubular shape, as shown in FIG. 7. The length of the piece is about 24-27 inches to match the length of the nitinol tubing used to create the device. In this case, the device to be created is a self-expanding stent. The width of the strip is sufficient to achieve a coiled sleeve having an outside diameter of about 0.1005 inches with about a 20° overlap when coiled in its maximum outside diameter. The coiled sleeve can be rolled or coiled in order to achieve a minimum outside diameter of about 0.095 inches. Thus, the range of expected inside diameters for the nitinol tubing would be from 0.095 to 0.1005 inches. It should be appreciated that the various sizes of the strips used to create the coiled sleeves will depend upon the various size of the tubular member which will eventually be formed into the desired device.

Figure 11:
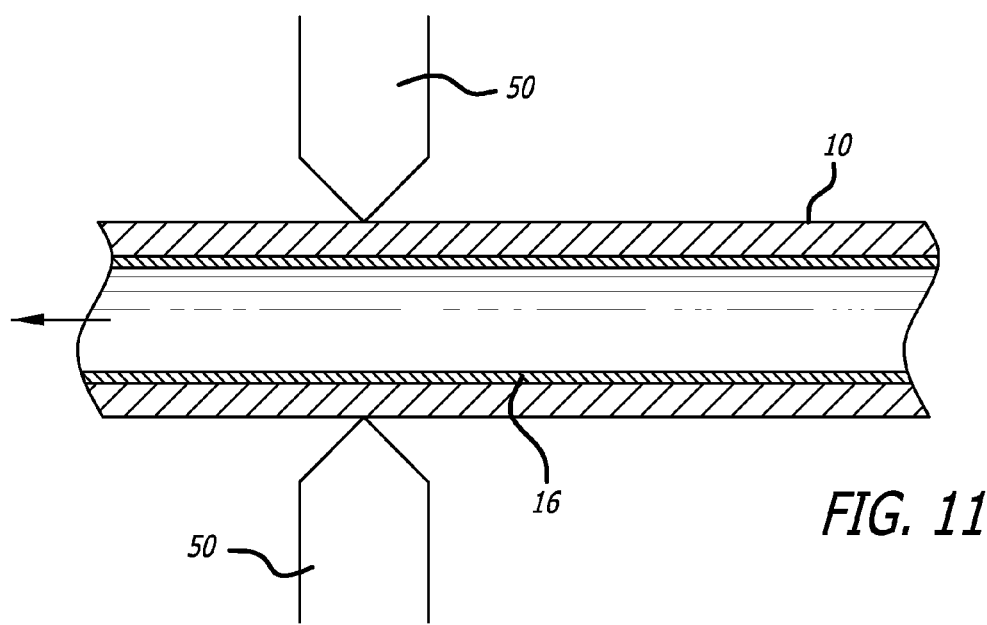
FIG. 11 is a cross-sectional view showing a disposable sacrificial mask and tubular member which undergo a co-drawing process prior to laser cutting.

In another aspect of the present invention, the process of making the device includes placing a sleeve made from a removable sacrificial material within the lumen of the tubular sleeve and co drawing the tubular member and sleeve together. FIG. 11 schematically shows the sleeve 16 and tubular member being drawn together through a die 50. Still other ways of co drawing the sleeve and tubular member can be achieved. In this aspect of the invention, the co drawing causes the surfaces of the sleeve and tubular member to come close together such that small spaces or gaps between the surfaces are eliminated or greatly reduced. The co-drawing of the tubular member and sleeve should be controlled to prevent the surfaces from molecularly bonding to each other. The tubular member and sleeve could then be laser cut with any remaining portion of sleeve being removed from the tubular member. In one aspect, the removal of any remaining portion of the sleeve can be done mechanically. In another aspect, the removal can be done chemically. In one particular aspect, any remaining portion of the sleeve cab be chemically removed from the tubular member by applying a chemical solution to the tubular member and sacrificial material for a time duration in which the chemical solution primarily attacks the sacrificial material. The sleeve can be made from any of the materials listed above.

Figure 12:
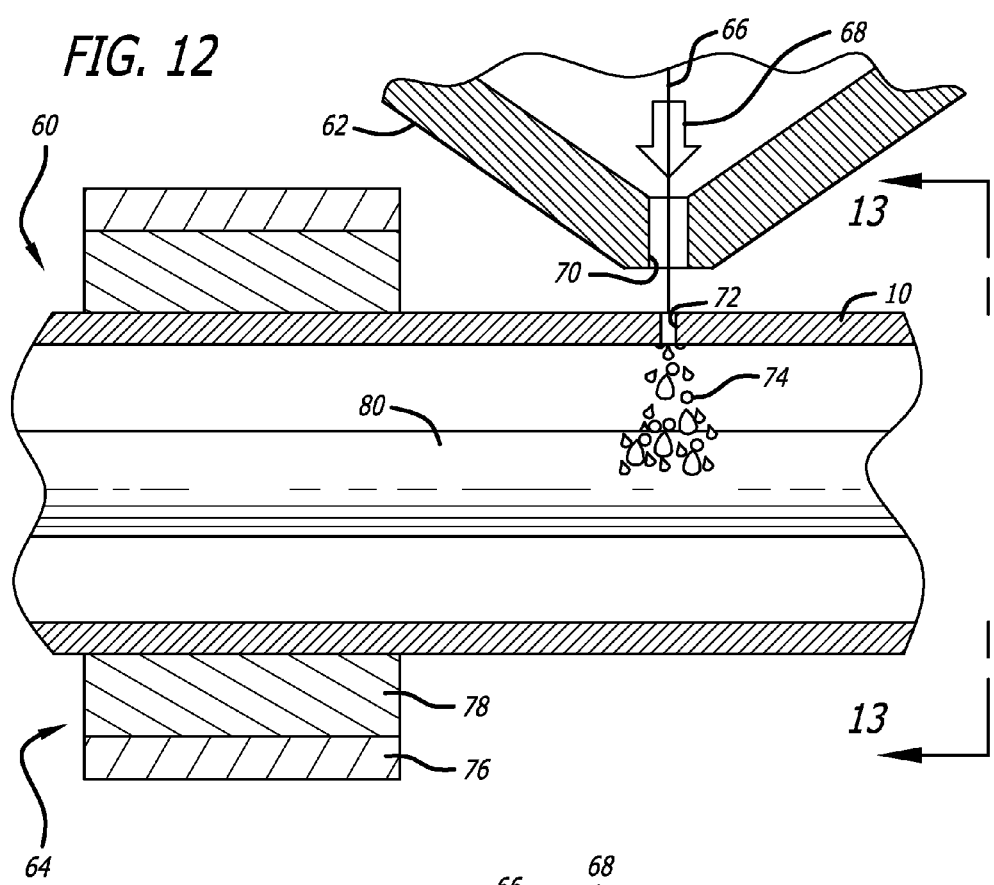
FIG. 12 is a cross-sectional schematic representation showing a system which applies ultrasonic energy to the tubular member during laser cutting.
Figure 13:
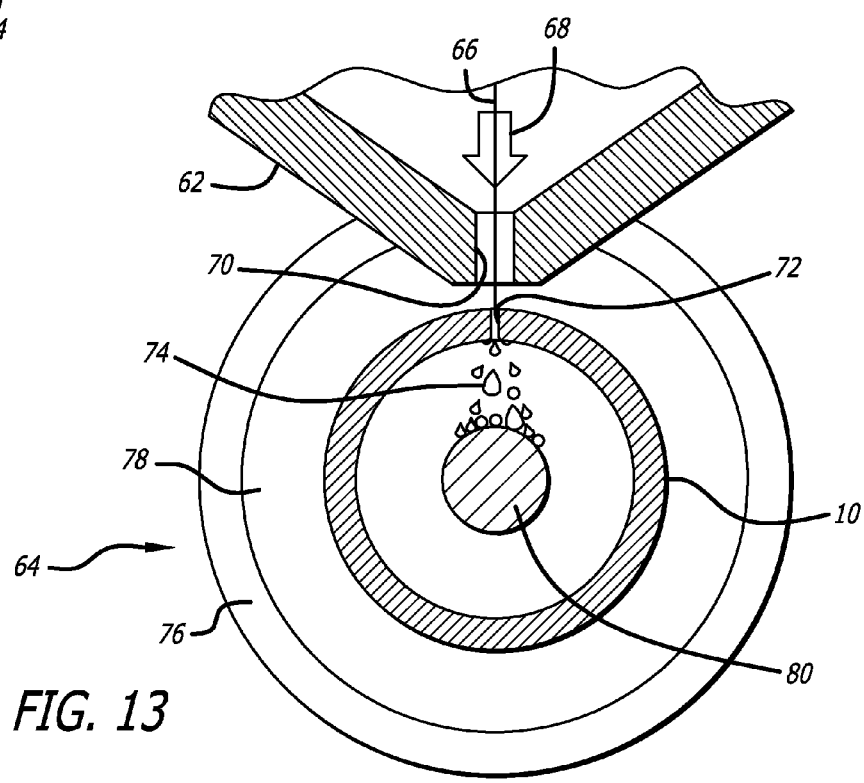
FIG. 13 is a cross-sectional view showing the system of FIG. 12 along line 13-13.

Referring now to FIGS. 12 and 13, another system 60 for dealing with the problems associated with molten slag adhering to the workpiece is disclosed. The system 60 utilizes the application of ultrasonic energy to the tubular member 10 as it is being laser cut to help prevent any slag from solidify or strongly adhering to an exposed surface of the tubular member. The system 60 includes a laser cutting apparatus 62, shown schematically in the drawing figures, along with an apparatus 64 for applying ultrasonic energy to the tubular member 10 as the tubular member 10 is being laser cut. The ultrasonic apparatus uses high frequency energy to vibrate both the liquidified slag and the tubular member 10 to produce reduce the ability of the slag from strongly adhering to the exposed portions of the tubular member. When liquids are exposed to these high frequency vibrations, both physical and chemical changes occur as a result of a physical phenomenon, known as cavitation. Cavitation is the formation, expansion, and implosion of microscopic gas bubbles in liquid as the molecules in the liquid absorb ultrasonic energy. If the vibration is sufficiently intense, it should break the attractive forces in the existing molecules of the slag and reduce its ability to bond to a surface.

In this aspect of the present invention, the laser cutting system 60 is shown using a conventional laser cutting apparatus 62 which utilizes air or oxygen to create the slots or kerfs extending through the wall of the tubular member 10. Additionally, the laser cutting apparatus 62 could pressurized inert gas, such as argon or helium, as is disclosed herein. In accordance with the present invention, still other laser cutting equipment could also be used to cut the tubular member 10.

Generally, as is schematically depicted in FIGS. 12 and 13, a laser beam 66 locally heats the tubular member 10 while the pressurized medium, depicted by arrow 68, is blown through a small coaxial orifice 70 directly onto the heated region in order to create the slots or kerfs 72. During the cutting process, slag 74 will form and will adhere to any exposed surface of the tubular member. The ultrasonic energy apparatus 64 helps to prevent this from occurring by applying ultrasonic energy directly to the tubular member 10, and any generated slag 74, to help prevent the slag from solidifying on any exposed surface of the tubular member 10.

As is shown schematically in FIGS. 12 and 13, the ultrasonic energy generating apparatus 64 includes an ultrasonic transducer 76 which is coupled to a bushing 78. This bushing 78 is, in turn, coupled to the tubular member 10 which will be laser cut by the laser apparatus 62. When subjected to ultrasonic energy, the slag 74 should either harmlessly fall from the surface of the tubular member or should be minimally bonded to the tubular member 10. In other words, the ultrasonic energy will help to prevent the slag 74 from "welding" itself to the surface of the tubular member 10. If the slag 74 becomes only minimally bonded, it should be easier to remove from the surface of the tubular member 10 using, for example, mechanical and/or chemical removal techniques, such as those described above.

The system 60 also utilizes an internal mandrel 80, or other component, which could be placed within the lumen of the tubular member 10 to help catch some of the slag 74 before it hits an exposed surface of the tubular member. The mandrel 80 can be made, for example, from copper. Additionally, in the method and system disclosed in FIGS. 12 and 13, only the tubular member 10 is shown being cut by the laser cutting apparatus 62. It should also be appreciated that a sacrificial mask, made in accordance with the present invention, could also be used with the tubular member 10 to further prevent slag from adhering to the finished workpiece.

The present embodiment shows the ultrasonic energy generating apparatus 64 as a simple transducer/bushing assembly. However, it will be appreciated by those skilled in the art that other structures could be utilized to apply the ultrasonic energy to the tubular member 10 as it is being laser cut without departing from the spirit and scope of the present invention. For these reasons, the present invention is not limited to the ultrasonic energy generating apparatus disclosed in the this particular embodiment.

Referring now to FIGS. 14 and 15, another apparatus which can be used in post-cutting procedures is disclosed. These figures show a compressed air mounting apparatus 90 which can be used to clean the surface of the tubular member 10 of slag and other impurities after the tubular member 10 has been cut. The compressed air mounting apparatus includes a length of tubing 92 having numerous outlet openings 94 which are in fluid communication with the lumen (not shown) of the tubing 92. One end 96 of the tubing 92 is coupled to a fitting 98 which is, in turn, attached to a compressed air supply 100. The other end 102 of the tubing 92 can be closed.

In use, the compressed air supply 100 provides an amply supply of compressed air which shoots out of the outlet openings 94 to create multiple jets of air which strike the surface of the laser-cut tubular member 10, shown mounted on the tubing 92 of the apparatus 90 in FIG. 15. The laser-cut tubular member 10 would be slidable on the tubing 92 so that the jets of air will strike the surface to remove any slag 104 or foreign particles (sometimes referred to as "islands"). The apparatus 90 could be encased within a housing 106 to contain the particles of slag 104 which will be blown off of the workpiece. It should be appreciated that other gases and fluids besides air could be used as the medium for this apparatus 90.

While the invention has been illustrated and described herein, in terms of methods for fabricating a medical device, such as an intravascular stent, it will be apparent to those skilled in the art that the methods can be used with other devices. Further, other modifications and improvements can be made without departing from the scope of the present invention.

We claim:

1. A method for making a device, the method comprising:
   providing a tubular member with an inner lumen which will be formed into the device;
   placing a sleeve made from a removable sacrificial material within the lumen of the tubular sleeve;
   co drawing the tubular member and sleeve together such that the surfaces of the sleeve and tubular member contact each other but are not molecularly bonded to each other;
   selectively removing a portion of the tubular member and sacrificial material using a laser device; and
   removing any remaining portion of the sleeve from the tubular member.

2. The method of claim 1, wherein any remaining portion of the sleeve is mechanically removed from the tubular member.

3. The method of claim 1, wherein any remaining portion of the sleeve is chemically removed from the tubular member.

4. The method of claim 1, wherein the tubular member is made from a nickel titanium alloy.

5. The method of claim 1, wherein co drawing of the sleeve and tubular member reduces any gaps that were existing between the surface of the sleeve and the surface of the tubular member.

6. The method of claim 3, wherein any remaining portion of the sleeve is chemically removed from the tubular member by applying a chemical solution to the tubular member and sacrificial material for a time duration in which the chemical solution primarily attacks the sacrificial material.

* * * * *